United States Patent
Buelo et al.

(10) Patent No.: US 11,529,295 B2
(45) Date of Patent: Dec. 20, 2022

(54) ORAL CARE COMPOSITION

(71) Applicant: Church & Dwight Co., Inc., Princeton, NJ (US)

(72) Inventors: Adonis R. Buelo, Leonardo, NJ (US); Elena Petrovicova, Princeton, NJ (US); Anthony Cirigliano, Chesterfield, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 17/031,480

(22) Filed: Sep. 24, 2020

(65) Prior Publication Data

US 2021/0085574 A1    Mar. 25, 2021

Related U.S. Application Data

(60) Provisional application No. 62/905,879, filed on Sep. 25, 2019.

(51) Int. Cl.

| | | |
|---|---|---|
| *A61K 8/21* | (2006.01) | |
| *A61K 8/24* | (2006.01) | |
| *A61K 8/23* | (2006.01) | |
| *A61K 8/365* | (2006.01) | |
| *A61K 8/86* | (2006.01) | |
| *A61Q 11/00* | (2006.01) | |
| *A61K 8/34* | (2006.01) | |

(52) U.S. Cl.
CPC .................. *A61K 8/21* (2013.01); *A61K 8/23* (2013.01); *A61K 8/24* (2013.01); *A61K 8/345* (2013.01); *A61K 8/365* (2013.01); *A61K 8/86* (2013.01); *A61Q 11/00* (2013.01); *A61K 2800/592* (2013.01); *A61K 2800/92* (2013.01)

(58) Field of Classification Search
CPC ... A61K 7/16; A61K 8/21; A61K 8/24; A61K 8/23; A61K 8/365; A61Q 11/00
USPC ............................................. 424/49, 52, 57
See application file for complete search history.

(56) References Cited

U.S. PATENT DOCUMENTS

| | | |
|---|---|---|
| 5,268,167 A | 12/1993 | Tung |
| 5,571,502 A | 11/1996 | Winston et al. |
| 5,603,922 A | 2/1997 | Winston et al. |
| 5,614,175 A | 3/1997 | Winston et al. |
| 5,817,296 A | 10/1998 | Winston et al. |
| 5,833,957 A | 11/1998 | Winston et al. |
| 6,120,754 A | 9/2000 | Lee et al. |
| 6,471,946 B1 | 10/2002 | Takatsuka et al. |
| 6,485,708 B1 | 11/2002 | Winston et al. |
| 6,740,311 B2 | 5/2004 | White, Jr. et al. |
| 6,863,882 B2 | 3/2005 | Dixon, Jr. et al. |
| 7,182,937 B2 | 2/2007 | Xu et al. |
| 7,662,363 B2 | 2/2010 | Stanier et al. |
| 8,911,712 B2 | 12/2014 | Buelo et al. |
| 9,180,318 B2 | 11/2015 | Deng et al. |
| 9,320,692 B2 | 4/2016 | Tung |
| 9,486,396 B2 | 11/2016 | Maloney et al. |
| 10,105,390 B2 | 10/2018 | Delgado Lopez et al. |
| 10,154,948 B2 | 12/2018 | Vemishetti et al. |
| 10,213,627 B2 | 2/2019 | Nowak et al. |
| 10,342,750 B2 | 7/2019 | Prencipe et al. |
| 10,357,438 B2 | 7/2019 | Jaracz et al. |
| 2003/0215401 A1 | 11/2003 | Estrada et al. |
| 2004/0022747 A1 | 2/2004 | Fisher et al. |
| 2004/0047814 A1 | 3/2004 | Xu et al. |
| 2004/0247535 A1 | 12/2004 | Kang et al. |
| 2006/0002865 A1* | 1/2006 | Buelo ....................... A61K 8/19 424/53 |
| 2007/0237725 A1 | 10/2007 | Tancredi et al. |
| 2008/0171001 A1 | 7/2008 | Engelman et al. |
| 2008/0292565 A1 | 11/2008 | Tung |
| 2010/0215593 A1* | 8/2010 | Reynolds ............... A61Q 11/00 424/57 |
| 2012/0315226 A1 | 12/2012 | Legeros et al. |
| 2012/0315228 A1 | 12/2012 | Deng et al. |
| 2015/0313813 A1 | 11/2015 | Rege et al. |
| 2016/0158283 A1 | 6/2016 | Reynolds |
| 2016/0303010 A1 | 10/2016 | Prencipe et al. |
| 2017/0020795 A1 | 1/2017 | Maloney et al. |
| 2017/0049671 A1 | 2/2017 | Prencipe et al. |
| 2017/0157003 A1 | 6/2017 | Mohan |

(Continued)

FOREIGN PATENT DOCUMENTS

| | | |
|---|---|---|
| CA | 2752337 | 7/2007 |
| CA | 2677324 | 8/2008 |

(Continued)

OTHER PUBLICATIONS

Tom's of Maine Natural Whole Care Toothpaste: Website at http://www.tomsofmaine.com/product-details/whole-care-toothpaste, which shows active and inactive ingredient list. Printed Oct. 28, 2020. US.

Ingram, et al., "Interactions of Fluoride and Non-Fluoride Agents with the Caries Process", Advances in Dental Research, vol. 8(2), pp. 158-165. Jul. 1994. US.

Stephen, et al., "A 3-year oral health dose-response study of sodium monofluoro-phosphate dentifrices with and without zinc citrate: anti-caries results", Community Dentistry and Oral Epidemiology, vol. 16, Issue 6, pp. 321-325. 1988. US.

Stephen K.W. et al., "In vivo Anticalculus Effect of a Dentifrice Containing 0.5% Zinc Citrate Trihydrate (Short Communication)" 1987, vol. 21, pp. 380-384.

*Primary Examiner* — Walter E Webb
(74) *Attorney, Agent, or Firm* — Church & Dwight Co., Inc.

(57) ABSTRACT

The present disclosure provides an oral care composition including a water-miscible base component, an amorphous calcium phosphate remineralizing component including a water-soluble or partially water-soluble calcium component and a water-soluble inorganic phosphate component, and a tartar control component, wherein the oral care composition provides enamel fluoride uptake activity and tartar control activity.

16 Claims, No Drawings

(56) References Cited

U.S. PATENT DOCUMENTS

| | | |
|---|---|---|
| 2018/0064757 A1 | 3/2018 | Lin et al. |
| 2018/0207076 A1 | 7/2018 | Kinscherf et al. |
| 2019/0269586 A1 | 9/2019 | Prencipe et al. |

FOREIGN PATENT DOCUMENTS

| | | |
|---|---|---|
| EP | 1178773 | 8/2005 |
| EP | 2556817 | 2/2013 |
| EP | 2583661 | 6/2016 |
| EP | 2544650 | 11/2016 |
| EP | 2794028 | 2/2017 |
| EP | 2349187 | 9/2017 |
| EP | 2699217 | 1/2018 |
| EP | 3033151 | 9/2018 |
| EP | 3294260 | 10/2019 |
| EP | 3294261 | 3/2020 |
| EP | 3148500 | 10/2020 |
| WO | 2000/000166 | 1/2000 |
| WO | WO 2018-099669 | 6/2018 |
| WO | WO 2019-034377 | 2/2019 |

* cited by examiner

ORAL CARE COMPOSITION

CROSS-REFERENCE TO RELATED APPLICATIONS

This application claims priority from U.S. Provisional Application No. 62/905,879, filed on Sep. 25, 2019, which application is hereby incorporated by reference in its entirety in this application.

FIELD OF THE INVENTION

The present disclosure relates to oral compositions useful for providing fluoride treatment with tartar control. More particularly, the disclosure relates to stable, amorphous calcium phosphate toothpaste formulations with tartar control.

BACKGROUND

This disclosure relates to a stable, amorphous calcium phosphate toothpaste formulation with tartar control.

Dental caries, i.e., tooth decay or cavities, is a leading cause of tooth damage in humans. Dental caries begins with lesions of so-called "white spots", which are demineralized areas below the surface of intact dental enamel. Such subsurface lesions are formed before a cavity is detectable. If unchecked, surface enamel above a subsurface lesion eventually collapses, leading to cavitations and subsequent loss of tooth structure.

The primary component of the enamel and dentin in teeth is calcium phosphate in the form of calcium hydroxyapatite. Restoration of a carious tooth to its original state involves the process of remineralization. The object of remineralization is to deposit hydroxyapatite in the carious lesion such that the dental enamel incorporates the hydroxyapatite into its structure at the point of lesion. Thus, remineralization not only prevents further tooth decay but also restores the tooth to its original state.

Saliva contains calcium and phosphate ions, which can help protect teeth against demineralization and can slowly remineralize teeth that have become demineralized by acids. Amorphous Calcium Phosphate (ACP) can be used in toothpastes and rinses to enhance the natural remineralization process. For ACP technology to work, available calcium and phosphate ions need to be introduced to enhance fluoride availability.

Plaque and tartar control toothpastes and rinses can contain gentle abrasive agents and surfactants to help remove plaque and tartar deposits on teeth, thereby whitening teeth. Tetrasodium Pyrophosphate (TSPP) is a primary anti-tartar agent known in the art. The mode of action of TSPP is to stabilize the calcium level in the saliva and interfere with growth of crystals that help form calculus. TSPP is an excellent calcium scavenger, but this property renders TSPP incompatible with ACP because it will negate the effectiveness of the ACP technology, which requires the introduction of calcium and phosphate ions.

U.S. Pat. App. Pub. No. 2004/0247535 describes an oral composition containing potassium phosphates. U.S. Pat. App. Pub. No. 2003/0215401 to Estrada et al. refers to a dental composition for reducing dentinal hypersensitivity due to the presence of exposed dentinal surface and open dentinal tubules, comprising a suitable carrier and a synergistic combination of: a desensitizing amount of at least one tubule blocking agent; and a nerve desensitizing agent selected from the group consisting of at least one potassium salt, at least one strontium salt, and mixtures thereof. U.S. Pat. App. Pub. No. 2004/0047814 to Xu et al. describes a composition for reducing dentinal hypersensitivity and remineralizing exposed dentinal surface and open dentinal tubules. The compositions described therein include calcium salts. U.S. Pat. Pub. No. 2004/0022747 to Fisher et al. describes a dental composition which purportedly eliminates or substantially reduces the discomfort and pain associated with dentinal hypersensitivity, exhibits enhanced anticaries and remineralization benefits, and includes a fluoride ion and a potassium ion releasable salt. The compositions described in each of these patent applications do not include a tartar control component, or even mention tartar control.

U.S. Pat. No. 5,268,167 to Tung describes the use of amorphous calcium compounds for use in remineralizing teeth. U.S. Pat. No. 5,268,167 to Tung describes the use of amorphous calcium compounds for use in remineralizing teeth. U.S. Pat. No. 5,603,922 to Winston et al. describes a composition for remineralization by applying a calcium salt, an additional divalent metal salt, and a phosphate salt. U.S. Pat. No. 5,614,175 to Winston et al. refers to mineralizing tubules of dentin thereby counteracting hypersensitivity. The mineralization is achieved by applying water soluble calcium salt and water soluble phosphate salt. U.S. Pat. No. 5,571,502 to Winston et al. refers to mineralizing tubules of dentin thereby counteracting hypersensitivity. The mineralization is achieved by applying water soluble calcium salt and water soluble phosphate salt. U.S. Pat. No. 5,817,296 to Winston et al. refers to mineralizing tubules of dentin thereby counteracting hypersensitivity. The mineralization is achieved by applying water soluble calcium salt and water soluble phosphate salt. The compositions described in each of these patents do not include a tartar control component, or even mention tartar control.

Accordingly, there is a still a desire and a need to provide an oral care composition that comprises ACP and an anti-tartar agent that does not negate the effectiveness of the ACP technology.

SUMMARY

In one or more embodiments, the present disclosure provides oral care compositions comprising ACP and an anti-tartar agent that does not negate the effectiveness of the ACP technology. Zinc citrate trihydrate demonstrated to be a viable agent to control tartar build up. It was surprisingly demonstrated that zinc citrate trihydrate will have little or no impact on calcium ions, and therefore, when used in ACP toothpaste formulations described herein will not have a negative impact on Enamel Fluoride Uptake, which can be assessed by Fluoride Uptake Study, FDA monograph evaluation (FDA Method #40).

The invention includes, without limitation, the following embodiments.

Embodiment 1: An oral care composition comprising: a water-miscible base component;
an amorphous calcium phosphate remineralizing component comprising a water-soluble or partially water-soluble calcium component and a water-soluble inorganic phosphate component; and a tartar control component; wherein the oral care composition provides enamel fluoride uptake activity and tartar control activity.

Embodiment 2: The oral care composition of Embodiment 1, wherein the tartar control component is zinc citrate trihydrate.

Embodiment 3: The oral care composition of any one of Embodiments 1-2, wherein the water-soluble or partially water-soluble calcium component is selected from the group consisting of calcium chloride, calcium bromide, calcium sulfate, calcium nitrate, calcium acetate, calcium gluconate, calcium benzoate, calcium glycerophosphate, calcium formate, calcium fumarate, calcium lactate, calcium butyrate and calcium isobutyrate, calcium malate, calcium maleate, calcium propionate, calcium valerate, and combinations thereof.

Embodiment 4: The oral care composition of any one of Embodiments 1-3, wherein the water-soluble or partially water-soluble calcium component is calcium sulfate.

Embodiment 5: The oral care composition of any one of Embodiments 1-4, wherein the water-soluble inorganic phosphate component is selected from the group consisting of potassium orthophosphate, sodium orthophosphate, ammonium orthophosphate, monopotassium phosphate, dipotassium phosphate, tripotassium phosphate, monosodium phosphate, disodium phosphate, trisodium phosphate, and combinations thereof.

Embodiment 6: The oral care composition of any one of Embodiments 1-5, wherein the water-soluble inorganic phosphate component is dipotassium phosphate.

Embodiment 7: The oral care composition of any one of Embodiments 1-6, wherein the water-soluble inorganic phosphate component is potassium phosphate.

Embodiment 8: The oral care composition of any one of Embodiments 1-7, wherein the amorphous calcium phosphate remineralizing component comprises about 0.05 wt. % to about 15 wt. % of the water-soluble or partially water-soluble calcium component, based on the total weight of the amorphous calcium phosphate remineralizing component.

Embodiment 9: The oral care composition of any one of Embodiments 1-8, wherein the amorphous calcium phosphate remineralizing component comprises about 0.05 wt. % to about 15 wt. % of the water-soluble inorganic phosphate component, based on the total weight of the amorphous calcium phosphate remineralizing component.

Embodiment 10: The oral care composition of any one of Embodiments 1-9, wherein the amorphous calcium phosphate remineralizing component further comprises a soluble fluoride salt capable of yielding fluoride ions.

Embodiment 11: The oral care composition of Embodiment 10, wherein the soluble fluoride salt is present in an amount of about 0.01 wt. % to about 5.0 wt. %, based on the total weight of the amorphous calcium phosphate remineralizing component.

Embodiment 12: The oral care composition of any one of Embodiments 1-11, wherein the amorphous calcium phosphate remineralizing component is present in an amount of about 0.1 to about 20 weight percent, based on the total weight of the oral care composition.

Embodiment 13: The oral care composition of any one of Embodiments 1-12, wherein the amorphous calcium phosphate remineralizing component is configured to have a pH in the range of about 4.5 to about 10.0 when the amorphous calcium phosphate remineralizing component is contacted with water or saliva.

Embodiment 14: The oral care composition of any one of Embodiments 1-13, wherein a molar ratio of calcium ions to phosphate ions in the amorphous calcium phosphate remineralizing component is between about 0.01:1 and about 100:1.

Embodiment 15: The oral care composition of any one of Embodiments 1-14, wherein the water-miscible base component comprises a compound from the group consisting of polyethylene glycol (PEG), glycerin, propylene glycol, sorbitol, and combinations thereof.

Embodiment 16: The oral care composition of any one of Embodiments 1-15, wherein the water-miscible base component is present in an amount in the range of about 20 to about 90 weight percent, based on the total weight of the oral care composition.

Embodiment 17: The oral care composition of any one of Embodiments 1-16, wherein the tartar control component is present in an amount in the range of about 0.1 wt. % to about 20 wt. %, based on the total weight of the oral care composition.

Embodiment 18: The oral care composition of any one of Embodiments 1-17, wherein the oral care composition provides an enamel fluoride concentration increase of at least about 1200 ppm, as assessed by Fluoride Uptake Study, FDA monograph evaluation (FDA Method #40).

Embodiment 19: The oral care composition of any one of Embodiments 1-18, wherein the water-soluble or partially water-soluble calcium component is present in an amount in the range of about 0.05 wt. % to about 5 wt. %, based on the total weight of the oral care composition.

Embodiment 20: The oral care composition of any one of Embodiments 1-19, wherein the water-soluble inorganic phosphate component is present in an amount in the range of about 0.05 wt. % to about 5 wt. %, based on the total weight of the oral care composition.

Embodiment 21: The oral care composition of any one of Embodiments 1-20, wherein the amorphous calcium phosphate remineralizing component further comprises a soluble fluoride salt capable of yielding fluoride ions, and wherein the soluble fluoride salt is present in an amount of about 0.01 wt. % to about 5.0 wt. %, based on the total weight of the oral care composition.

Embodiment 22: A method for providing simultaneous fluoride uptake activity and tartar control activity comprising administering an oral care composition according to any of Embodiments 1-21 to the teeth of a user.

Embodiment 23: Use of an oral care composition according to any of Embodiments 1-21 for providing simultaneous fluoride uptake activity and tartar control activity.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

Other aspects and advantages of the present disclosure will become apparent from the following.

DETAILED DESCRIPTION

The present disclosure now will be described more fully hereinafter. The disclosure may be embodied in many different forms and should not be construed as limited to the embodiments set forth herein; rather, these embodiments are provided so that this disclosure will satisfy applicable legal requirements. Like numbers refer to like elements throughout. As used in this specification and the claims, the singular forms "a," "an," and "the" include plural references unless the context clearly dictates otherwise.

In one or more aspects, the present disclosure provides oral care compositions comprising ACP and an anti-tartar agent. The oral care composition can be in the form of a mouthwash, powder, toothpaste or gel, chewing gum, lozenge, and the like.

In various embodiments of the present invention, the oral care composition comprises a remineralizing component, which can be useful to help remedy and/or help prevent dental caries. The remineralizing component can comprise at least one water-soluble or partially water-soluble calcium compound and at least one water-soluble inorganic phosphate compound, and optionally, at least one water-soluble fluorine compound. The ingredients are formulated into a single-part component, such that the ingredients do not react with one another to cause premature precipitation of calcium phosphate until introduced into the oral cavity. See, e.g., the remineralizing components described in U.S. Pat. No. 8,911,712 to Buelo et al., which is herein incorporated by reference. In various embodiments, the remineralizing component is Amorphous Calcium Phosphate (ACP).

In various embodiments, the remineralizing component comprises a water-soluble or partially water-soluble calcium component selected from the group consisting of calcium chloride, calcium bromide, calcium sulfate, calcium nitrate, calcium acetate, calcium gluconate, calcium benzoate, calcium glycerophosphate, calcium formate, calcium fumarate, calcium lactate, calcium butyrate and calcium isobutyrate, calcium malate, calcium maleate, calcium propionate, calcium valerate, and combinations thereof. The calcium compound is considered to be water-soluble when at least 0.25 gram thereof dissolves in 100 ml of $H_2O$ at 20° C. In the compositions of the disclosure for the remineralization of human dental enamel, at least about 100 ppm of calcium ions should be present; the upper limit is about 35,000 ppm of calcium ions.

As used herein, the term "partially water-soluble" with respect to the calcium salt component refers to a calcium salt having a solubility such that the salt is capable of releasing more than about 40 ppm but no more than about 1400 ppm of calcium cations in an aqueous solution having a pH of about 7.0 at a temperature of about 25° C. Preferably, the calcium salt(s) used in this invention has a solubility in aqueous solution such that the salt(s) releases from about 100 ppm to no more than about 1400 ppm of calcium cations. In certain embodiments, the remineralizing component comprises calcium sulfate.

The term "water-soluble" as used herein with respect to the phosphate, fluoride and divalent metal salts suitable for use in the present disclosure refers to a solubility such that the salts are each capable of releasing at least about 1400 ppm of ions into an aqueous solution having a temperature of about 25° C. and a pH of about 7.0.

In various embodiments, the remineralizing component comprises a water-soluble or partially water-soluble phosphate component. In some embodiments, the phosphate component can include alkali salts and ammonium salts of orthophosphoric acid. For example, in some embodiments, the phosphate component is selected from the group consisting of potassium orthophosphate, sodium orthophosphate, ammonium orthophosphate, monopotassium phosphate, dipotassium phosphate, tripotassium phosphate, monosodium phosphate, disodium phosphate, trisodium phosphate, and combinations thereof.

The concentration of the phosphate ions can be in the range of about 100 ppm to 40,000 ppm, and its solubility in water is defined as in the case of the calcium compounds. In certain embodiments, the phosphate component is dipotassium phosphate.

In some embodiments, the remineralizing component can comprise water-soluble salts yielding both calcium and phosphate ions, such as monobasic-calcium orthophosphate.

In some embodiments, the remineralizing component comprises a water-soluble fluoride component. The fluoride component can comprise alkali fluorides, fluorozirconates, fluorosilicates, fluoroborates, fluorostannites, organic fluorides, water-soluble alkali metal monofluorophosphates, and combinations thereof. In various embodiments, the fluoride component comprises a component from the group consisting of sodium, potassium, lithium fluoride, ammonium fluoride, tin fluoride, indium fluoride, zirconium fluoride, copper fluoride, nickel fluoride, palladium fluoride, sodium fluorozirconate, potassium fluorozirconate, ammonium fluorozirconate, tin fluorozirconate, sodium monofluorophosphate, lithium monofluorophosphate, potassium monofluorophosphate, ammonium monofluorophosphate, aluminum monofluorophosphate, and combinations thereof.

In certain embodiments, the remineralizing component comprises about 0.05 wt. % to 15 wt. %, or about 0.10 wt. % to 10 wt. % of calcium salt yielding calcium ions, based on the total weight of the remineralizing component. In various embodiments, a calcium salt is present in the oral care composition in an amount in the range of about 0.05 wt. % to about 5.0 wt. %, or about 0.10 wt. % to about 3.0 wt. %, based on the total weight of the oral care composition. In various embodiments, the calcium salt is present in the oral care composition in an amount sufficient to yield about 0.01 to about 3.0 wt. % calcium ions, or about 0.1 to about 1.0 wt. % calcium ions, based on the total weight of the oral care composition. In some embodiments, the remineralizing component comprises from about 0.05 wt. % to 15 wt. %, or about 0.10 wt. % to 10 wt. %, of a water-soluble phosphate salt yielding phosphate ions, based on the total weight of the remineralizing component. In various embodiments, a phosphate salt is present in the oral care composition in an amount in the range of about 0.05 wt. % to about 5 wt. %, or about 0.10 wt. % to about 3 wt. %, based on the total weight of the oral care composition. In various embodiments, the phosphate salt is present in the oral care composition in an amount sufficient to yield about 0.01 to about 3.0 wt. % phosphate ions, or about 0.1 to about 1.0 wt. % phosphate ions, based on the total weight of the oral care composition. In some embodiments, the remineralizing component comprises from about 0.01 wt. % to 5.0 wt. %, or about 0.02 wt. % to 2.0 wt. %, of a soluble fluoride salt yielding fluoride ions, based on the total weight of the remineralizing component. In various embodiments, a fluoride salt is present in the oral care composition in an amount in the range of about 0.01 wt. % to about 5 wt. %, or about 0.10 wt. % to about 3 wt. %, based on the total weight of the oral care composition. In various embodiments, the fluoride salt is present in the oral care composition in an amount sufficient to yield about 0.01 to about 3.0 wt. % fluoride ions, or about 0.5 to about 1.0 wt. % fluoride ions, based on the total weight of the oral care composition.

In various embodiments, when the calcium, phosphate, and optional fluoride salts are contacted with water or saliva, the pH of the remineralizing component is between about 4.5 and 10.0, or between about 5.0 and 7.0. The pH of the remineralization component may be adjusted to the pH desired by methods well known in the art.

In some embodiments, the molar ratio of calcium and phosphate ions in the remineralizing agent is between about 0.01 to 1 and about 100 to 1, between about 0.2 to 1 and about 5 to 1, or between about 1 to 1 and about 1.67 to 1. In certain embodiments, for example, the remineralizing component comprises calcium sulfate in an amount of about 1.5-3.0 wt. %, potassium phosphate in an amount of about 0.1-1.0 wt. %, and sodium fluoride in an amount of about 0.1-0.5 wt. %, wherein all weight percentages are based on the total weight of the oral care composition.

In certain embodiments, the remineralizing component can be present in the oral care composition in amounts in the range of about 0.1 to about 20 weight percent, about 1 to about 10 weight percent, or about 2 to about 5 weight percent, based on the total weight of the oral care composition. In certain embodiments, the remineralizing component can be present in an amount of at least about 0.1 weight percent, at least about 1 weight percent, or at least about 3 weight percent, based on the total weight of the oral care composition (e.g., with a maximum concentration of about 20 percent by weight).

In various embodiments of the present invention, the oral care composition can comprise a tartar control component. In various embodiments, the tartar control component is zinc citrate trihydrate. The tartar control component can be present in an amount of about 0.1 wt. % to about 20 wt. %, about 0.5 wt. % to about 15 wt. %, or about 1.0 wt. % to about 10 wt. %, based on the total weight of the oral care composition.

In some embodiments, the oral care composition can comprise a water-miscible base component. In various embodiments of the present disclosure, the water-miscible base component of the oral compositions described herein can comprise polyethylene glycol (PEG), glycerin, propylene glycol, sorbitol, and combinations thereof. For example, in some embodiments the base component comprises polyethylene glycol (PEG). In certain embodiments, the base component comprises PEG-8.

In certain embodiments, the water-miscible base component can be present in amounts in the range of about 20 to about 90 weight percent, about 25 to about 60 weight percent, about 30 to about 50 weight percent, or about 35 to about 45 weight percent, based on the total weight of the oral care composition. In certain embodiments, the base component can be present in an amount of at least about 15 weight percent, at least about 20 weight percent, at least about 30 weight percent, at least about 40 weight percent, or at least about 50 weight percent, based on the total weight of the oral care composition (e.g., with a maximum concentration of about 90 percent by weight).

In various embodiments, the oral care composition can further comprise one or more additional ingredients. For example, the oral care composition can comprise at least one of a sweetener and a flavoring agent. In certain embodiments, the one or more sweeteners and/or flavoring agents can comprise sodium saccharin, monoammonium glycyrrhizate, a preferred flavor component, and combinations thereof.

In some embodiments, a sweetener can be present in an amount in the range of about 0.01 to about 5 weight percent, about 0.05 to about 2 weight percent, about 0.1 to about 1 weight percent, or about 0.2 to about 0.5 weight percent, based on the total weight of the oral care composition. In various embodiments, a sweetener can be present in an amount of at least about 0.01 weight percent, at least about 0.1 weight percent, or at least about 0.5 weight percent, based on the total weight of the oral care composition (e.g., with a maximum concentration of about 10 weight percent). In some embodiments, one or more flavoring agents can be present in an amount in the range of about 0.01 to about 10 weight percent, about 0.05 to about 5 weight percent, about 0.1 to about 2 weight percent, or about 0.5 to about 1 weight percent, based on the total weight of the oral care composition. The flavoring agent(s) can be present in an amount of at least about 0.01 weight percent, at least about 0.5 weight percent, at least about 1 weight percent, or at least about 2 weight percent, based on the total weigh of the oral care composition (e.g., with a maximum concentration of about 10 weight percent).

In some embodiments, the oral care composition can comprise a viscosity modifier, one or more surfactants, a thickening component, and/or other additives. See, e.g., the additional components described in U.S. Pat. No. 8,911,712 to Buelo et al., which is herein incorporated by reference.

As described above, in various embodiments, the oral care composition can be in the form of a mouthwash, powder, toothpaste or gel, chewing gum, lozenge, and the like. The oral care compositions described herein can be manufactured in the form of a final oral care product having a desired dosage size, shape and weight via mixing and packing processes known in the art.

EXAMPLES

Example 1

Two embodiments of an oral care composition (referred to as "Formula 1" and "Formula 2") according to the present disclosure are provided. Table 1 below provides ingredients included in an embodiment of the oral care composition of the present disclosure. Table 1 also includes the weight percentage of each ingredient, based on the total weight of the oral care composition.

TABLE 1

Oral Care Composition-Formula 1 and Formula 2

| Ingredient | Wt. % Formula 1 | Wt. % Formula 2 |
| --- | --- | --- |
| PEG/PPG 116/66 copolymer (Pluracare L-1220) | 0.1-5.0 | 0.1-5.0 |
| PEG/PPG 38/8 copolymer (Pluracare L4370) | 35.2070 | n/a |
| PEG-8 | 0.5-2.0 | 0.5-35.0 |
| Glycerin | n/a | 5.0-15.0 |
| Sodium Bicarbonate | 10.0-60.0 | 10.0-60.0 |
| Sodium Fluoride, milled | 0.01-2.0 | 0.01-2.0 |
| Sodium Saccharin Powder | 0.5-2.0 | 0.5-2.0 |
| Titanium Dioxide | n/a | 0.05-1.0 |
| Zinc Citrate Trihydrate | 0.1-2.0 | 0.1-2.0 |
| Aerosil 200VS | 2.00 | 0.25 |
| Hydrated Silica | n/a | 5.0-25.0 |
| Silica | n/a | 0.1-5.0 |
| Sodium Lauryl Sulfate | 0.5-2.0 | 0.5-2.0 |
| Flavor | 0.5-2 | 0.5-2 |
| Sodium Carbonate | n/a | 0.1-1.0 |
| Calcium Sulfate | 0.5-4.0 | 0.5-4.0 |
| Potassium Phosphate | 0.5-2.0 | n/a |
| Dipotassium Phosphate | n/a | 0.5-2.0 |

It is noted that Formula 1 and Formula 2 are each in the form of a toothpaste gel.

Example 2

Formulas 1 and 2, according to Example 1 above, are assessed by Fluoride Uptake Study, FDA monograph evaluation (FDA Method #40). A Control Formula, Placebo Formula, and USP Toothpaste Standard Formula are also assessed for comparison. The Placebo Formula does not include a remineralizing agent (i.e., no fluoride treatment). The Control Formula includes an ACP remineralizing agent, but does not include a tartar control agent. The USP Toothpaste Standard Formula includes an industry standard fluoride treatment agent, but does not include ACP.

Sound, upper, central, bovine incisors were selected and cleaned of all adhering soft tissue. A core of enamel 3 mm in diameter was prepared from each tooth by cutting perpendicular to the labial surface with a hollow-core diamond drill bit. This was performed under water to prevent overheating of the specimens. Each specimen was embedded in the end of a plexiglass rod (114" diameter×2" long) using methylmethacrylate. The excess acrylic was cut away exposing the enamel surface. The enamel specimens were polished with 600 grit wet/dry paper and then with microtine Gamma Alumina. The resulting specimen was a 3 mm disk of enamel with all but the exposed surface covered with acrylic.

Each enamel specimen was then etched by immersion into 0.5 ml of 1M HC104 for 15 seconds. Throughout the etch period the etch solutions were continuously agitated. A sample of each solution was then buffered with TISAB to a pH of 5.2 (0.25 ml sample, 0.5 ml TISAB and 0.25 ml 1N NaOH) and the fluoride content determined by comparison to a similarly prepared standard curve (1 ml std and 1 ml TISAB). For use in depth of etch calculation, the Ca content of the etch solution was determined by taking 50 $\mu l$ and analyzing for Ca by atomic absorption (0.05 ml qs to 5 ml). These data were the indigenous fluoride level of each specimen prior to treatment.

The specimens were once again ground and polished as described above. An incipient lesion was formed in each enamel specimen by immersion into a 0.1M lactic acid/0.2% Carbopol 907 solution for 24 hours at room temperature. These specimens were then rinsed well with distilled water and stored in a humid environment until used.

The treatments were performed using supernatants of the dentifrice slurries. The slurries consisted of 1 part dentifrice and 3 parts (9 g:27 ml, w/w) deionized water. The slurries were mixed well and then centrifuged at 10,000 rpm (−16,000 g) for 10 minutes. The specimens were then immersed into 25 ml of their assigned supernatant with constant stirring (350 rpm) for 30 minutes. Following treatment, the specimens were rinsed with distilled water. One layer of enamel was then removed from each specimen and analyzed for fluoride and calcium as outlined above (i.e., 15 second etch). The pretreatment fluoride (indigenous) level of each specimen was then subtracted from the post treatment value to determine the change in enamel fluoride due to the test treatment.

Table 2 below shows the results of the assessment of Formula 1 compared to the Control Formula, Placebo Formula, and USP Toothpaste Standard Formula. As is known in the art, an increase in the enamel fluoride concentration is desired.

TABLE 2

Enamel Fluoride Concentration Before and After Application

| Toothpaste Formula | Enamel Fluoride Concentration (ppm) | | |
| --- | --- | --- | --- |
| | Pre Treatment | Post Treatment | Increase |
| Placebo (No Fluoride) | 51 ± 5* | 68 ± 5 | 18 ± 2 |
| USP Toothpaste Std (Fluoride other than ACP) | 48 ± 4 | 1245 ± 28 | 1197 ± 28 |
| Formula 1 (ACP + 0.5% Zinc Citrate) | 46 ± 3 | 1496 ± 50 | 1450 ± 49 |
| Control (ACP, no tartar control) | 58 ± 5 | 1908 ± 58 | 1851 ± 56 |

*Mean ± SEM (N = 12)

Table 3 below shows the results of the assessment of Formula 2 compared to the Control Formula, Placebo Formula, and USP Toothpaste Standard Formula. As is known in the art, an increase in the enamel fluoride concentration is desired.

TABLE 3

Enamel Fluoride Concentration Before and After Application

| Toothpaste Formula | Enamel Fluoride Concentration (ppm) | | |
| --- | --- | --- | --- |
| | Pre Treatment | Post Treatment | Increase |
| Placebo (No Fluoride) | 41 ± 3* | 82 ± 6 | 41 ± 6 |
| USP Toothpaste Std (Fluoride other than ACP) | 39 ± 4 | 1374 ± 36 | 1334 ± 35 |
| Formula 2 (ACP + 0.5% Zinc Citrate) | 41 ± 2 | 1753 ± 53 | 1713 ± 53 |
| Control (ACP, no tartar control) | 42 ± 4 | 1872 ± 48 | 1830 ± 50 |

As expected, the Control Formula without fluoride treatment was significantly less effective in promoting enamel fluoride uptake than the other 3 formulas. Experimental Formulas 1 and 2 and the Control Formula were significantly more effective in promoting enamel fluoride uptake than the USP Toothpaste Std Formula, indicating that ACP is a more effective remineralizing component as compared to remineralizing component used in the industry standard fluoride toothpaste formula.

Experimental Formulas 1 and 2 demonstrated only a slightly less enamel fluoride uptake than the Control Formula, indicating that zinc citrate trihydrate, when used in an ACP toothpaste formulation for tartar control, will not have a significant negative impact on Enamel Fluoride Uptake. It is noted, as stated above, that the experimental formulas demonstrated higher enamel fluoride uptake than required by the industry standard for a formulation classified as a fluoride treatment formulation.

Many modifications and other embodiments of the disclosure will come to mind to one skilled in the art to which this disclosure pertains having the benefit of the teachings presented in the foregoing description; and it will be apparent to those skilled in the art that variations and modifications of the present disclosure can be made without departing from the scope or spirit of the disclosure. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An oral care composition comprising:
    a water-miscible base component;
    an amorphous calcium phosphate remineralizing component comprising a water-soluble or partially water-soluble calcium component, a water-soluble inorganic phosphate component, and a soluble fluoride salt that yields fluoride ions; and
    a tartar control component in an amount effective to control tartar buildup on teeth without significantly impacting release of calcium ions from the amorphous calcium phosphate remineralizing component, the tartar control component comprising zinc citrate trihydrate;
    wherein the oral care composition is effective for fluoride uptake in teeth such that it provides an enamel fluoride concentration increase of at least 1200 ppm, as assessed by Fluoride Uptake Study, FDA monograph evaluation (FDA Method #40) while simultaneously providing tartar control activity.

2. The oral care composition of claim 1, wherein the water-soluble or partially water-soluble calcium component is selected from the group consisting of calcium chloride, calcium bromide, calcium sulfate, calcium nitrate, calcium acetate, calcium gluconate, calcium benzoate, calcium glycerophosphate, calcium formate, calcium fumarate, calcium lactate, calcium butyrate and calcium isobutyrate, calcium malate, calcium maleate, calcium propionate, calcium valerate, and combinations thereof.

3. The oral care composition of claim 1, wherein the water-soluble or partially water-soluble calcium component is calcium sulfate.

4. The oral care composition of claim 1, wherein the water-soluble inorganic phosphate component is selected from the group consisting of potassium orthophosphate, sodium orthophosphate, ammonium orthophosphate, monopotassium phosphate, dipotassium phosphate, tripotassium phosphate, monosodium phosphate, disodium phosphate, trisodium phosphate, and combinations thereof.

5. The oral care composition of claim 1, wherein the water-soluble inorganic phosphate component is dipotassium phosphate.

6. The oral care composition of claim 1, wherein the water-soluble inorganic phosphate component is potassium phosphate.

7. The oral care composition of claim 1, wherein the water-soluble or partially water-soluble calcium component is present in an amount in the range of about 0.05 wt. % to about 5 wt. %, based on the total weight of the oral care composition.

8. The oral care composition of claim 1, wherein the water-soluble inorganic phosphate component is present in an amount in the range of about 0.05 wt. % to about 5 wt. %, based on the total weight of the oral care composition.

9. The oral care composition of claim 1, wherein the soluble fluoride salt is present in an amount of about 0.01 wt. % to about 5.0 wt. %, based on the total weight of the oral care composition.

10. The oral care composition of claim 1, wherein the amorphous calcium phosphate remineralizing component is present in an amount of about 0.1 to about 20 weight percent, based on the total weight of the oral care composition.

11. The oral care composition of claim 1, wherein the amorphous calcium phosphate remineralizing component is configured to have provide the oral care composition with a pH in the range of about 4.5 to about 10.0 when the amorphous calcium phosphate remineralizing component is contacted with water or saliva.

12. The oral care composition of claim 1, wherein a molar ratio of calcium ions to phosphate ions in the amorphous calcium phosphate remineralizing component is between about 0.01:1 and about 100:1.

13. The oral care composition of claim 1, wherein the water-miscible base component comprises a compound from the group consisting of polyethylene glycol (PEG), glycerin, propylene glycol, sorbitol, and combinations thereof.

14. The oral care composition of claim 1, wherein the water-miscible base component is present in an amount in the range of about 20 to about 90 weight percent, based on the total weight of the oral care composition.

15. The oral care composition of claim 1, wherein the tartar control component is present in an amount in the range of about 0.1 wt. % to about 20 wt. %, based on the total weight of the oral care composition.

16. A method for providing simultaneous fluoride uptake activity and tartar control activity comprising administering an oral care composition according to claim 1 to the teeth of a user.

* * * * *